United States Patent
Doering et al.

(10) Patent No.: US 9,981,149 B2
(45) Date of Patent: May 29, 2018

(54) HIGHLY ACTIVE ANTIPERSPIRANT WITH IMPROVED SKIN TOLERABILITY

(71) Applicant: Henkel AG & Co. KGaA, Duesseldorf (DE)

(72) Inventors: Thomas Doering, Dormagen (DE); Natascha Schevardo, Erkrath (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days. days.

(21) Appl. No.: 15/614,845

(22) Filed: Jun. 6, 2017

(65) Prior Publication Data

US 2017/0348551 A1    Dec. 7, 2017

(30) Foreign Application Priority Data

Jun. 7, 2016  (DE) .................. 10 2016 210 037

(51) Int. Cl.
| | | |
|---|---|---|
| *A61Q 15/00* | (2006.01) | |
| *A61K 8/28* | (2006.01) | |
| *A61K 8/26* | (2006.01) | |
| *A61K 8/36* | (2006.01) | |
| *A61K 8/58* | (2006.01) | |

(52) U.S. Cl.
CPC ............. *A61Q 15/00* (2013.01); *A61K 8/26* (2013.01); *A61K 8/28* (2013.01); *A61K 8/36* (2013.01); *A61K 8/585* (2013.01); *A61K 2800/874* (2013.01)

(58) Field of Classification Search
None
See application file for complete search history.

(56) References Cited

U.S. PATENT DOCUMENTS

| | | |
|---|---|---|
| 4,775,528 A | 10/1988 | Callaghan et al. |
| 6,010,688 A | 1/2000 | Shen |
| 6,042,816 A | 3/2000 | Shen |
| 6,245,325 B1 | 6/2001 | Shen |
| 6,436,381 B1 | 8/2002 | Carrillo et al. |
| 6,649,152 B2 | 11/2003 | Carrillo et al. |
| 6,923,952 B2 | 8/2005 | Allen et al. |
| 2004/0265255 A1 | 12/2004 | Holerca et al. |
| 2005/0208013 A1 | 9/2005 | Yamaguchi et al. |

FOREIGN PATENT DOCUMENTS

| | | |
|---|---|---|
| GB | 1549617 A | 8/1979 |
| GB | 2048229 A | 12/1980 |
| WO | 2013105924 A2 | 7/2013 |

OTHER PUBLICATIONS

Intellectual Property Office, Search Report under Section 17(5) issued in UK Application No. 1709073.9 dated Dec. 8, 2017.
Kirk-Othmer, "Diuretics to Emulsions", Encyclopedia of Chemical Technology, third edition, vol. 8, 1979, pp. 913-916, John Wiley & Sons, Inc., USA.

*Primary Examiner* — Robert A Wax
*Assistant Examiner* — Randeep Singh
(74) *Attorney, Agent, or Firm* — Lorenz & Kopf LLP

(57) ABSTRACT

Antiperspirant compositions that are suitable in particular for application with a roller applicator and contain water, at least one antiperspirant aluminum-zirconium-glycine complex and also L-valine, wherein the weight ratio of glycine to L-valine is in the range of about 20:1 to about 4:1, have a high antiperspirant efficacy and are tolerated very well on the skin at the same time.

18 Claims, No Drawings

HIGHLY ACTIVE ANTIPERSPIRANT WITH IMPROVED SKIN TOLERABILITY

CROSS-REFERENCE TO RELATED APPLICATION

This application claims priority to German Patent Application No. 10 2016 210 037.8, filed Jun. 7, 2016, which is incorporated herein by reference in its entirety.

TECHNICAL FIELD

The present patent application relates to water-based antiperspirant compositions, referred to synonymously as antiperspirant compositions, preferably those suitable for application to the skin using a roller applicator and having improved skin tolerability, while at the same time also having a strong antiperspirant effect.

BACKGROUND

There are numerous possibilities for applying antiperspirant compositions to the skin. Stick compositions having a stable shape are spread over the skin using a stick dispenser until an effective amount has been applied. Gels and creams can also be applied with stick-type dispensers, which are applied to the skin using a dispenser surface. For antiperspirant and/or deodorant compositions for the axillary area in particular, numerous different forms of application have been developed, mainly sprays and roll-on compositions that contain propellant gas and those that are free of propellant gas, in addition to those already mentioned. In the case of roll-on preparations that are free of propellant gas, a slightly thickened fluid is applied by means of a rotatably mounted ball by rolling it over the skin. Antiperspirant roll-on compositions may be water-based or oil-based. For example, the oil-based preparation of the usual antiperspirant sprays is also suitable for administration as a roll-on preparation. In this case, the antiperspirant active ingredient is in the form of a powder suspended in oil, the oil being thickened with a lipophilic gelling agent to prevent separation of the powder particles. However, such roll-ons are hardly represented in the market. The usual antiperspirant roll-on compositions are water-based, i.e., they contain water in an amount of approx. 50 wt % or more, based on their total weight. The antiperspirant active ingredient, usually an antiperspirant aluminum or aluminum zirconium compound, is present in dissolved form.

The hygiene routine of many users includes regular shaving of the underarm area before applying an antiperspirant or deodorant, but application of an ethanol-based agent to freshly shaved skin can cause a great deal of burning. With regular use, such agents dry the skin and thus make it more sensitive and easily irritated.

WO 2013/105924 A2 discloses an anhydrous oral hygiene composition containing a zirconium-amino acid complex, for example, a zirconium-alanine complex, which is suspended in a hydrophobic vehicle and is suitable for treatment of hypersensitive teeth.

EP 1161589 B1 discloses a liquid deodorant with a high deodorizing effect, which is at the same time gentle on textiles and contains 80 to 99 wt % water, 0.1 to 2.0 wt % of a component comprising quaternary ammonium groups or amine oxide groups and one or two C8-C22 alk(en)yl groups in the molecule, and a buffer solution, which is adjusted with an acid that may be valine and an alkalizing agent to a pH in the alkaline range of 7.5 to 9.5. However, antiperspirant compositions containing highly effective aluminum zirconium compounds must have an acidic pH, preferably a pH in the range of 3.0 to 4.5, especially preferably in the range of 3.4 to 4.0, measured at 20° C. In the neutral and alkaline range, the aluminum zirconium compounds would hydrolyze to form less active hydroxides.

BRIEF SUMMARY

Antiperspirant compositions and methods for improving skin tolerability of antiperspirant compositions are provided herein. In an exemplary embodiment, an antiperspirant composition includes water, at least one antiperspirant aluminum-zirconium-glycine complex, and L-valine. The weight ratio of glycine to L-valine is from about 20:1 to about 4:1.

In another exemplary embodiment, a method includes using L-valine to improve skin tolerability of an antiperspirant composition. The antiperspirant composition includes water and at least one antiperspirant aluminum-zirconium-glycine complex. The method includes incorporating the L-valine into the antiperspirant composition such that the weight ratio of glycine to L-valine is from about 20:1 to about 4:1.

DETAILED DESCRIPTION

The following detailed description is merely exemplary in nature and is not intended to limit the present disclosure or the application and uses of the subject matter as described herein. Furthermore, there is no intention to be bound by any theory presented in the preceding background or the following detailed description.

One object of the present patent application was to supply water-based antiperspirant compositions, in particular roll-ons that have a high antiperspirant efficacy with the greatest possible skin tolerability.

It has surprisingly been found that the object described above is achieved by adding selected amounts of L-valine to an aqueous solution of an antiperspirant aluminum-zirconium-glycine complex.

The subject matter of the present patent application is therefore an antiperspirant composition containing:
a) water,
b) at least one antiperspirant aluminum-zirconium-glycine complex,
c) L-valine,
characterized in that the weight ratio of glycine to L-valine is in the range of about 20:1 to about 4:1.

Additionally preferred embodiments of the compositions according to the present disclosure can be found in the dependent claims.

Water Content

The compositions according to the present disclosure preferably contain about 40% to about 90 wt %, especially preferably about 50% to about 85 wt %, extremely preferably about 60% to about 80 wt %, more extremely preferably about 65% to about 75 wt % water, each based on the total weight of the composition. The phrase "with water" in the sense of the present patent application is understood to mean "free water," i.e., water that is not present in the form of water of crystallization, water of hydration or similar molecularly bound water in the antiperspirant composition. The water of crystallization, water of hydration or the similar molecularly bound water present in the components that are used, in particular in the antiperspirant active ingredients, does not amount to free water in the sense of the present patent application. Free water is water that is present as a solvent, for example, or as a solvent constituent of other active ingredients in the composition according to the present disclosure.

"Normal conditions" in the sense of the present patent application include a temperature of about 20° C. (measured reference temperature) and a pressure of about 1013 mbar. Melting point specifications are also based on a pressure of about 1013 mbar.

Antiperspirant Aluminum-Zirconium-Glycine Complex

Preferred antiperspirant aluminum-zirconium-glycine complexes according to the present disclosure are selected from aluminum zirconium trichlorohydrex glycine, aluminum zirconium tetrachlorohydrex glycine, aluminum zirconium pentachlorohydrex glycine and aluminum zirconium octachlorohydrex glycine as well as mixtures thereof.

Especially preferred antiperspirant active ingredients according to the present disclosure are selected from so-called "activated" aluminum-zirconium-glycine complexes, which are also referred to as antiperspirant active ingredients "with an enhanced activity." Such active ingredients are known in the state of the art and are also available commercially. Their production is described, for example, in GB Patent 2,048,229, U.S. Pat. No. 4,775,528 and U.S. Pat. No. 6,010,688. Activated aluminum zirconium salts are usually created by a heat treatment of a relatively dilute solution of the salt (for example, about 10 wt % salt) to increase its HPLC peak 4 to peak 3 area ratio. The activated salt may then be dried to form a powder, in particular by spray drying. In addition to spray drying, roller drying, for example, is also suitable.

Activated aluminum zirconium salts typically have an HPLC peak 4 to peak 3 area ratio of at least about 0.4, preferably at least about 0.7, especially preferably at least about 0.9, with at least about 70% of the aluminum being assigned to these peaks.

Activated aluminum zirconium salts need not necessarily be used as a spray-dried powder. Also preferred antiperspirant active ingredients according to the present disclosure are nonaqueous solutions of solubilizates of an activated antiperspirant aluminum zirconium salt, for example, according to U.S. Pat. No. 6,010,688, which are stabilized against the loss of activation due to the rapid degradation of the HPLC peak 4:peak 3 area ratio of the salt by adding an active amount of a polyvalent alcohol containing 3 to 6 carbon atoms and 3 to 6 hydroxyl groups, preferably propylene glycol, sorbitol and pentaerythritol.

Additional preferred antiperspirant active ingredients include activated aluminum zirconium salts such as those disclosed in U.S. Pat. No. 6,245,325 or U.S. Pat. No. 6,042,816, for example, containing about 5-about 78 wt % (USP) of an activated antiperspirant aluminum zirconium salt, an amino acid or hydroxyalkanoic acid in an amount sufficient to supply an (amino acid or hydroxyalkanoic acid) to (Al+Zr) weight ratio of about 2:1-about 1:20 and preferably about 1:1 to about 1:10, as well as a water-soluble calcium salt in an amount sufficient to supply a Ca:(Al+Zr) weight ratio of about 1:1-about 1:28 and preferably about 1:2-about 1:25. Especially preferred solid activated antiperspirant salt compositions, e.g., according to U.S. Pat. No. 6,245,325 or U.S. Pat. No. 6,042,816 contain about 48-about 78 wt % (USP), preferably about 66-about 75 wt % of an activated aluminum zirconium salt and about 1-about 16 wt %, preferably about 4-about 13 wt % molecularly-bound water (water of hydration), as well as enough water-soluble calcium salt that the Ca:(Al+Zr) weight ratio is about 1:1-about 1:28, preferably about 1:2-about 1:25, and enough amino acid, so that the amino acid to (Al+Zr) weight ratio is about 2:1-about 1:20, preferably about 1:1-about 1:10.

Additional particularly preferred solid antiperspirant activated salt compositions, for example, according to U.S. Pat. No. 6,245,325 or U.S. Pat. No. 6,042,816, contain about 48-about 78 wt % (USP), preferably about 66-about 75 wt % of an activated aluminum zirconium salt, and about 1-about 16 wt %, preferably about 4-about 13 wt % molecularly bound water (water of hydration), also enough water-soluble calcium salt so that the Ca:(Al+Zr) weight ratio is about 1:1-about 1:28, preferably about 1:2-about 1:25, and enough glycine so that the glycine to (Al+Zr) weight ratio is about 2:1-about 1:20, preferably about 1:1-about 1:10.

For the stabilization of the antiperspirant salts, preferred water-soluble calcium salts are selected from calcium chloride, calcium bromide, calcium nitrate, calcium citrate, calcium formate, calcium acetate, calcium gluconate, calcium ascorbate, calcium lactate, calcium glycinate, calcium carbonate, calcium sulfate, calcium hydroxide as well as mixtures thereof.

Preferred aluminum-zirconium-glycine complexes have an Al:Zr molar ratio of about 2 to about 10.

The antiperspirant active ingredients are present in dissolved form. The antiperspirant active ingredients may be used as nonaqueous solutions or as glycolic solubilizates.

Preferred aluminum-zirconium-glycine complexes have a molar metal-to-chloride ratio of about 0.9-about 1.3, preferably about 0.9-about 1.1, especially preferably about 0.9-about 1.0.

The aluminum-zirconium-glycine complexes contain the glycine to prevent polymerization of the zirconium species during synthesis. The amino acid is preferably present in the complex in an amount of about 1 to about 3 mol, especially preferably about 1.3-about 1.8 mol, each per mol zirconium.

In addition, aluminum zirconium chlorohydrate-glycine complexes, which are stabilized with betaine ((CH3)3N+-CH2-COO—), are also preferred according to the present disclosure. Especially preferred corresponding compounds have a total molar (betaine+glycine)/Zr ratio of (about 0.1-about 3.0):1, preferably (about 0.7-about 1.5):1 and a molar ratio of betaine to glycine of at least about 0.001:1. Corresponding compounds are disclosed in U.S. Pat. No. 7,105,691, for example.

In a particular preferred embodiment according to the present disclosure, a so-called "activated" salt, in particular a salt with a high HPLC peak 5 aluminum content, in particular with a peak 5 area of at least about 33%, especially preferably at least about 45%, based on the total area under the peaks 2-5, measured with HPLC of an about 10 wt % aqueous solution of the active ingredient under conditions under which the aluminum species are dissolved in at least four successive peaks (referred to as peaks 2-5). Preferred aluminum zirconium salts with a high HPLC peak 5 aluminum content (also referred to as "E5AZCH") are disclosed, for example, in U.S. Pat. No. 6,436,381 and U.S. Pat. No. 6,649,152.

In addition, preferred activated "E5AZCH" salts are those in which the HPLC peak 4 to peak 3 area ratio is at least about 0.4, preferably at least about 0.7, especially preferably at least about 0.9.

Additional particularly preferred antiperspirant active ingredients include those aluminum zirconium salts having a high HPLC peak 5 aluminum content, which are additionally stabilized with a water-soluble strontium salt and/or with a water-soluble calcium salt. Corresponding salts are disclosed in U.S. Pat. No. 6,923,952, for example.

Especially preferred compositions according to the present disclosure contain at least one antiperspirant aluminum-zirconium-glycine complex in a total amount of about 6-about 20 wt %, preferably about 10-about 16 wt % and especially preferably about 12-about 14 wt %, each based on the total weight of the active substance (USP), which is free of ligands and free of water of crystallization, in the antiperspirant composition.

The weight of glycine to L-valine according to the present disclosure is in the range of about 20:1 to about 4:1, preferably in the range of about 17:1 to about 5:1, especially preferably in the range of about 15:1 to about 10;1.

Preferred compositions according to the present disclosure contain about 0.01 to about 1 wt %, especially preferably about 0.05 to about 0.3 wt %, extraordinarily preferably about 0.1 to about 0.2 wt % L-valine, each based on the weight of the antiperspirant composition.

In principle D-valine is also suitable according to the present disclosure that is less preferred because of the inferior availability and the higher price.

According to the present disclosure it is preferable for the valine, in particular L-valine, not to be part or a ligand of an antiperspirant aluminum zirconium compound but instead to be present in free dissolved form in the composition according to an exemplary embodiment.

Preferred compositions according to the present disclosure contain at least one oleogel consisting of
i) at least one silicone elastomer,
ii) polymethylsilsesquioxane,
iii) at least one copolymer consisting of at least two monomers selected from the group formed from ethylene, propylene, butene and styrene as well as
iv) at least one hydrocarbon oil consisting only of C and H.

It has surprisingly been found that the addition of this oleogel greatly improves the drying of an aqueous composition on a surface treated with the composition.

Especially preferred compositions according to the present disclosure are characterized in that the at least one silicone elastomer selected from vinyl dimethicone/methicone silsesquioxane crosspolymer, dimethicone/vinyl dimethicone crosspolymer, dimethicone/phenyl vinyl dimethicone crosspolymer, stearyl vinyl/hydromethyl-siloxane copolymer, polysilicone-11, stearoxymethicone/dimethicone copolymer as well as mixtures thereof, especially preferably selected from vinyl dimethicone/methicone silsesquioxane crosspolymer.

Another obligatory component of the aforementioned oleogel is polymethylsilsesquioxane. Polymethylsilsesquioxane is a polymer formed by hydrolysis and condensation of methyl trimethoxysilane. It is preferably a powder. Polymethylsilsesquioxane preferably swells in oil and thickens this oil by forming an oleogel.

Another component of the aforementioned oleogel is a copolymer consisting of at least two monomers selected from the group formed from ethylene, propylene, butene and styrene. Extremely preferred compositions according to the present disclosure are characterized in that the at least one copolymer iii) is selected from ethylene/propylene copolymers, ethylene/propylene/styrene copolymers and butylene/ethylene/styrene copolymers as well as mixtures thereof, especially preferably selected from ethylene/propylene copolymers. The at least one copolymer iii) preferably swells in oil and thickens this oil by forming an oleogel.

Another obligatory component of the aforementioned oleogel is at least one hydrocarbon oil consisting only of C and H, i.e., only of hydrocarbon and hydrogen.

Preferred compositions according to the present disclosure contain at least one oil-in-water emulsifier with an HLB value greater than about 7 to about 20, selected especially preferably from nonionic oil-in-water emulsifiers with an HLB value from greater than about 7 up to about 20.

For example, these include the emulsifiers known in general to those skilled in the art such as those listed in Kirk-Othmer, "Encyclopedia of Chemical Technology," 3rd edition, 1979, vol. 8, pages 913-916. For ethoxylated products, the HLB value is calculated according to the formula HLB=(100−L):5, where L denotes the amount by weight of the lipophilic groups, i.e., the fatty alkyl groups or fatty acyl groups in the ethylene oxide adducts, expressed in % by weight.

Surfactants and emulsifiers in the sense of the present patent application are amphiphilic (bifunctional) compounds, which consist of at least one hydrophobic molecular part and at least one hydrophilic molecular part. The hydrophobic radical is preferably a hydrocarbon chain with 8-28 carbon atoms, which may be saturated or unsaturated, linear or branched. This C8-C28 alkyl chain is especially preferably linear. Basic properties of the surfactants and emulsifiers include the oriented absorption at interfaces as well as the aggregation to form micelles and the formation of lyotrophic phases.

Additional antiperspirant compositions preferred according to the present disclosure are characterized in that at least one nonionic emulsifier with an HLB value in the range of about 12-about 18 is included. Preferred antiperspirant compositions according to the present disclosure are characterized in that the nonionic oil-in-water emulsifiers with an HLB value of greater than about 7 up to about 20 selected from ethoxylated C8-C24 alkanols with an average of 10-100 mol ethylene oxide per mol, ethoxylated C8-C24 carboxylic acids with an average of 10-100 mol ethylene oxide per mol, with an average of 20-100 mol ethylene oxide per mol ethoxylated sorbitan monoesters of linear saturated and unsaturated C12-C30 carboxylic acids, which may be hydroxylated, in particular those of myristic acid, palmitic acid, stearic acid or mixtures of these fatty acids, silicone copolyols with ethylene oxide units or with ethylene oxide units and propylene oxide units, alkyl mono- and oligoglycosides with 8 to 22 carbon atoms in the alkyl radical and their ethoxylated analogs, ethoxylated sterols, partial esters of polyglycerols with n=2 to 10 glycerol units and esterified with 1 to 4 saturated or unsaturated, linear or branched, optionally hydroxylated C8-C30 fatty acid radicals if they have an HLB value of greater than about 7 up to about 20, as well as mixtures of the aforementioned substances.

Ethoxylated C8-C24 alkanols have the formula R1O(CH2CH2O)nH, where R1 stands for a linear or branched alkyl and/or alkenyl radical with 8-24 carbon atoms and n stands for the average number of ethylene oxide units per molecule, for numbers of 10 to 100, preferably 10 to 30 mol ethylene oxide on 1 mol capryl alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol as well as their technical grade mixtures. Adducts of 10-100 mol ethylene oxide onto technical grade fatty alcohols with 12-18 carbon atoms such as coconut, palm, palm kernel or tallow fatty alcohol are also suitable.

The ethoxylated C8-C24 carboxylic acid have the formula R1O(CH2CH2O)nH, where R1O stands for a linear or branched, saturated or unsaturated acyl radical with 8-24 carbon atoms and n stands for the average number of ethylene oxide units per molecule, for numbers of 10-100, preferably 10-30 mol ethylene oxide on 1 mol caprylic acid, 2-ethylhexanoic acid, capric acid, lauric acid, isotridecanoic acid, myristic acid, cetylic acid, palmitoleic acid, stearic acid, isostearic acid, oleic acid, elaidic acid, petroselinic acid, arachic acid, gadoleic acid, behenic acid, erucic acid and brassidic acid as well as their technical grade mixtures. Adducts of 10-100 mol ethylene oxide onto technical grade fatty acids with 12-18 carbon atoms, such as coconut, palm, palm kernel or tallow fatty acid, are also suitable. Especially preferred are PEG-50 monostearate, PEG-100 monostearate, PEG-50 monooleate, PEG-100 monooleate, PEG-50 monolaurate and PEG-100 monolaurate.

The C12-C18 alkanols or the C12-C18 carboxylic acids with 10-30 units of ethylene oxide per molecule as well as mixtures of these substances are especially preferred, in particular ceteth-10, ceteth-12, ceteth-20, ceteth-30, steareth-10, steareth-12, steareth-20, steareth-21, steareth-30, ceteareth-10, ceteareth-12, ceteareth-20, ceteareth-30, laureth-12 and beheneth-20.

Sorbitan monoesters of linear saturated and unsaturated C12-C30 carboxylic acids, which may be hydroxylated and are ethoxylated with an average of 20-100 mol ethylene oxide per mol, selected from polysorbate-20, polysorbate-40, polysorbate-60 and polysorbate-80 are preferred.

In addition, C8-C22 alkyl mono- and oligoglycosides are preferably used. C8-C22 alkyl mono- and oligoglycosides are known commercially available surfactants and emulsifiers. They are synthesized in particular by reacting glucose or oligosaccharides with primary alcohols having 8-22 carbon atoms. With respect to the glycoside radical, both monoglycosides, in which a cyclic sugar radical is glycosidically linked to the fatty alcohol, and oligomeric glycosides having a degree of oligomerization of approx. 8, preferably 1-2, are suitable. The degree of oligomerization is a statistical mean, based on the customary homolog distribution for such technical grade products. Products available under the brand name Plantacare® contain a glycosidically bound C8-C16 alkyl group on an oligoglucoside radical with a mean degree of oligomerization of 1-2, in particular 1.2-1.4. Particularly preferred C8-C22 alkyl mono- and oligoglycosides are selected from octyl glucoside, decyl glucoside, lauryl glucoside, palmityl glucoside, isostearyl glucoside, stearyl glucoside, arachidyl glucoside and behenyl glucoside as well as mixtures thereof. The acyl glucamides derived from glucamine are also suitable as nonionic oil-in-water emulsifiers.

Ethoxylated sterols, in particular ethoxylated soy sterols are oil-in-water emulsifiers that are suitable according to the present disclosure. The degree of ethoxylation must be more than 5, preferably at least 10, to have an HLB value greater than 7. Suitable commercial products include, for example, PEG-10 soy sterol, PEG-16 soy sterol and PEG-25 soy sterol.

In addition, partial esters of polyglycerols with 2 to 10 glycerol units and with 1 to 4 saturated or unsaturated linear or branched optionally hydroxylated C8-C30 fatty acid esters are esterified and used if they have an HLB value greater than 7 up to 20. Especially preferred are diglycerol monocaprylate, diglycerol monocaprate, diglycerol monolaurate, triglycerol monocaprylate, triglycerol monocaprate, triglycerol monolaurate, tetraglycerol monocaprylate, tetraglycerol monocaprate, tetraglycerol monolaurate, pentaglycerol monocaprylate, pentaglycerol monocaprate, pentaglycerol monolaurate, hexaglycerol monocaprylate, hexaglycerol monocaprate, hexaglycerol monolaurate, hexaglycerol monomyristate, hexaglycerol monostearate, decaglycerol monocaprylate, decaglycerol monocaprate, decaglycerol monolaurate, decaglycerol monomyristate, decaglycerol monoisostearate, decaglycerol monostearate, decaglycerol monooleate, decaglycerol monohydroxystearate, decaglycerol dicaprylate, decaglycerol dicaprate, decaglycerol dilaurate, decaglycerol dimyristate, decaglycerol diisostearate, decaglycerol distearate, decaglycerol dioleate, decaglycerol dihydroxystearate, decaglycerol tricaprylate, decaglycerol tricaprate, decaglycerol trilaurate, decaglycerol trimyristate, decaglycerol triisostearate, decaglycerol tristearate, decaglycerol trioleate and decaglycerol trihydroxystearate.

Especially preferred antiperspirant compositions according to the present disclosure contain at least one oil-in-water emulsifier with an HLB value of greater than about 7 up to about 20 in a total amount of about 0.5-about 5 wt %, preferably about 0.8-about 4 wt %, especially preferably about 1.2-about 3 wt % and extremely preferably about 1.5-about 2 wt %, each based on the total composition.

Additional antiperspirant compositions that are particularly preferred according to the present disclosure contain at least one nonionic oil-in-water emulsifier with an HLB value in the range of about 12-about 18 in a total amount of about 0.5-about 5 wt %, preferably about 0.8-about 4 wt %, especially preferably about 1.2-about 3 wt % and extremely preferably about 1.5-about 2 wt %, each based on the total composition.

Additional antiperspirant compositions that are particularly preferred according to the present disclosure and have an HLB value in the range of about 12-about 18, selected from linear saturated and unsaturated C12-C24 alkanols etherified with 7-40 ethylene oxide units per molecule, in a total amount of about 0.5-about 5 wt %, preferably about 0.8-about 4 wt %, especially preferably about 1.2-about 3 wt % and extremely preferably about 1.5-about 2 wt %, each based on the total composition. The aforementioned oil-in-water emulsifiers are especially preferably selected from Steareth, Ceteth, Myristeth, Laureth, Trideceth, Arachideth and Beheneth each with 7-40 ethylene oxide units per molecule, in particular Steareth-10, Steareth-20, Steareth-21, Steareth-30, Steareth-40, Ceteth-10, Ceteth-20, Ceteth-21, Ceteth-30, Ceteth-40, Laureth-10, Laureth-20, Laureth-30, Trideceth-10, Trideceth-20 and Trideceth-30 as well as mixtures thereof.

Additional antiperspirant compositions according to the present disclosure contain at least one nonionic oil-in-water emulsifier with an HLB value in the range of about 12-about 18, selected from Steareth-10, Steareth-20, Steareth-21, Steareth-30, Steareth-40, Ceteth-10, Ceteth-20, Ceteth-21, Ceteth-30, Ceteth-40, Laureth-10, Laureth-20, Laureth-30, Trideceth-10, Trideceth-20 and Trideceth-30 as well as mixture thereof in a total amount of about 0.5-about 5 wt %, preferably about 0.8-about 4 wt %, especially preferably about 1.2-about 3 wt % and extremely preferably about 1.5-about 2 wt %, each based on the total composition.

Additional antiperspirant compositions preferred according to the present disclosure contain at least one cosmetic oil and at least one oil-in-water emulsifier with an HLB value of more than about 7 up to about 20 and are in the form of an oil-in-water emulsion.

Especially preferred antiperspirant compositions according to the present disclosure are present as an oil-in-water emulsion and contain at least one oil-in-water emulsifier with an HLB value of greater than about 7 up to about 20 in a total amount of about 0.5-about 5 wt %, preferably about 0.8-about 4 wt %, especially about 1.2-about 3 wt % and extremely preferably about 1.5-about 2 wt %, each based on the total composition.

Additional preferred antiperspirant compositions that are especially preferred according to the present disclosure are in the form of an oil-in-water emulsion and contain at least one nonionic oil-in-water emulsifier with an HLB value in the range of about 12-about 18 in a total amount of about 0.5-about 5 wt %, preferably about 0.8-about 4 wt %, especially preferably about 1.2-about 3 wt % and extremely preferably about 1.5-about 2 wt %, each based on the total composition.

Additional antiperspirant compositions that are particularly preferred according to the present disclosure are in the form of an oil-in-water emulsion and contain at least one nonionic oil-in-water emulsifier with an HLB value in the range of about 12 to about 18, selected from a linear saturated and unsaturated C12-C24 alkanols etherified with 7 to 40 ethylene oxide units per molecule, in a total amount of about 0.5-about 5 wt %, preferably about 0.8-about 4 wt %, especially preferably about 1.2-about 3 wt % and extremely preferably about 1.5-about 2 wt %, each based on the total composition. The aforementioned oil-in-water emulsifiers are especially preferably selected from Steareth, Ceteth, Myristeth, Laureth, Trideceth, Arachideth and Beheneth each with 7 to 40 ethylene oxide units per molecule, in particular Steareth-10, Steareth-20, Steareth-21, Steareth-30, Steareth-40, Ceteth-10, Ceteth-20, Ceteth-21, Ceteth-30, Ceteth-40, Laureth-10, Laureth-20, Laureth-30, Trideceth-10, Trideceth-20 and Trideceth-30 as well as mixtures thereof.

Additional preferred antiperspirant compositions according to the present disclosure are in the form of an oil-in-water emulsion and contain at least one nonionic oil-in-water emulsifier with an HLB value in the range of about 12 to about 18, selected from Steareth-10, Steareth-20, Steareth-21, Steareth-30, Steareth-40, Ceteth-10, Ceteth-20, Ceteth-21, Ceteth-30, Ceteth-40, Laureth-10, Laureth-20, Laureth-30, Trideceth-10, Trideceth-20 and Trideceth-30 as well as mixture thereof, in a total amount of about 0.5-about 5 wt %, preferably about 0.8-about 4 wt %, especially preferably about 1.2-about 3 wt % and extremely preferably about 1.5-about 2 wt %, each based on the total composition.

Water-in-Oil Emulsifiers

Additional preferred antiperspirant compositions according to the present disclosure contain at least one water-in-oil emulsifier, preferably at least nonionic water-in-oil emulsifier, each with an HLB value greater than about 1.0 and less than or equal to about 7.0, preferably in the range of about 3-about 6. Examples of a few of these water-in-oil emulsifiers are listed in Kirk-Othmer, Encyclopedia of Chemical Technology, 3rd edition, 1979, vol. 8, page 913. As already mentioned, the HLB value can also be calculated for ethoxylated adducts.

The following are preferred as the water-in-oil emulsifier:
Linear or branched saturated or unsaturated C12-C30 alkanols each etherified with 1 to 4 ethylene oxide units per molecule, which are extremely preferably obtained from steareth, ceteth, myristeth, laureth, trideceth, arachideth and beheneth, each with 1 to 4 ethylene oxide units per molecule, in particular steareth-2, steareth-3, steareth-4, ceteth-2, ceteth-3, ceteth-4, myristeth-2, myristeth-3, myristeth-4, laureth-2, laureth-3, laureth-4, trideceth-2, trideceth-3 and trideceth-4 as well as mixtures thereof;
Linear saturated alkanols with 12 to 30 carbon atoms, in particular 16 to 22 carbon atoms, in particular cetyl alcohol, stearyl alcohol, arachidyl alcohol, behenyl alcohol and lanolin alcohol or mixtures of these alcohols, such as those obtainable in technical grade hydrogenation of vegetable and animal fatty acids;
Esters and in particular partial esters of a polyol with 2 to 6 carbon atoms and linear saturated and unsaturated fatty acids with 12 to 30, in particular 14 to 22 carbon atoms, which may be hydroxylated. Such esters or partial esters include, for example, the mono- and diesters of glycerol or ethylene glycol or the monoesters of propylene glycol with linear saturated and unsaturated $C_{12}$-$C_{30}$ carboxylic acids that may be hydroxylated, in particular those with palmitic acid and stearic acid, the sorbitan mono-, di- or triesters of linear, saturated and unsaturated $C_{12}$-$C_{30}$ carboxylic acids, which may be hydroxylated, in particular those of myristic acid, palmitic acid, stearic acid or mixtures of these fatty acids, the pentaerythrityl mono-, di-, tri- and tetraesters and the methyl glucose mono- and diesters of linear, saturated and unsaturated $C_{12}$-$C_{30}$ carboxylic acids, which may be hydroxylated; of these, especially preferred are the mono-, di-, tri- and tetraesters of pentaerythritol with linear saturated fatty acids with 12 to 30, in particular 14 to 22 carbon atoms, which may be hydroxylated, as well as mixtures thereof. Especially preferred according to the present disclosure are the mono- and diesters. Preferred $C_{12}$-$C_{30}$ fatty acid radicals according to the present disclosure are selected from lauric acid, myristic acid, palmitic acid, stearic acid, arachic acid and behenic acid radicals. The stearic acid radical is especially preferred. Especially preferred nonionic water-in-oil emulsifiers according to the present disclosure with an HLB value of greater than about 1.0 and less than or greater than about 7.0 are selected from glyceryl monostearate, glyceryl distearate, glyceryl monopalmitate, glyceryl dipalmitate and mixtures thereof;
Sterols, i.e., steroids, having a hydroxyl group on the $C_3$ atom of the steroid backbone and isolated from animal tissue (zoosterols, e.g., cholesterol, lanosterol) as well as plants (phytosterols, e.g., ergosterol, stigmasterol, sitosterol) and from yeasts and fungi (mycosterols), and which may have a low degree of ethoxylation (1 to 5 EO);
Alkanols and carboxylic acids, each with 8 to 24 carbon atoms, in particular with 16 to 22 carbon atoms in the alkyl group and 1 to 4 ethylene oxide units per molecule, having an HLB value of greater than about 1.0 and less than or equal to about 7.0;
Glycerol monoethers of saturated and/or unsaturated, branched and/or unbranched alcohols with a chain length of 8 to 30, in particular 12 to 18 carbon atoms;
Partial esters of polyglycerols with n=2 to 10 glycerol units and esterified with 1 to 5 saturated or unsaturated, linear or branched, optionally hydroxylated $C_8$-$C_{30}$ fatty acid radicals if they have an HLB value greater than 1.0 to less than or equal to 7,
as well as mixtures of the aforementioned substances.

The at least one water-in-oil emulsifier with an HLB value of greater than about 1.0 and less than or equal to about 7.0, preferably in a range of about 3 to about 6, is especially preferably selected from linear or branched, saturated or unsaturated C12-C30 alkanols, etherified with 1 to 4 ethylene oxide units per molecule, which is extraordinarily preferred, is selected from steareth, ceteth, myristeth, laureth, trideceth, arachideth and beheneth each with 1 to 4 ethylene oxide units per molecule, in particular steareth-2, steareth-3, steareth-4, ceteth-2, ceteth-3, ceteth-4, myristeth-2, myristeth-3, myristeth-4, laureth-2, laureth-3, laureth-4, trideceth-2, trideceth-3 and trideceth-4 as well as mixtures thereof.

According to the present disclosure, it may be preferable to use only a single water-in-oil emulsifier. In another preferred embodiment, the compositions according to the present disclosure contain mixtures in particular technical grade mixtures of at least two water-in-oil emulsifiers.

Preferred antiperspirant compositions according to the present disclosure will contain at least one water-in-oil emulsifier with an HLB value of greater than about 1.0 and less than or equal to about 7.0, preferably in the range of about 3 to about 6 in a total amount of about 1.8-about 3 wt %, preferably about 2-about 2.8 wt % and especially preferably about 2.4-about 2.6 wt %, each based on the total weight of the composition according to an exemplary embodiment.

Additional antiperspirant compositions that are preferred according to the present disclosure contain at least one nonionic water-in-oil emulsifier with an HLB value in the range of about 3 to about 6 selected from steareth-2, steareth-3, steareth-4, ceteth-2, ceteth-3, ceteth-4, myristeth-2, myristeth-3, myristeth-4, laureth-2, laureth-3, laureth-4, trideceth-2, trideceth-3 and trideceth-4 as well as mixtures thereof, in a total amount of about 1.8-about 3 wt %, preferably about 2-about 2.8 wt % and especially preferably about 2.4-about 2.6 wt %, each based on the total weight of the composition according to an exemplary embodiment.

Additional antiperspirant compositions that are preferred according to the present disclosure are in the form of an oil-in-water emulsion and contain at least one water-in-oil emulsifier with an HLB value greater than about 1.0 and less than or equal to about 7.0, preferably in the range of about 3 to about 6 in a total amount of about 1.8-about 3 wt %, preferably about 2-about 2.8 wt % and especially preferably about 2.4-about 2.6 wt %, each based on the total weight of the composition according to an exemplary embodiment.

Additional antiperspirant compositions that are preferred according to the present disclosure are in the form of oil-in-water emulsions and contain at least one nonionic water-in-oil emulsifier with an HLB value in the range of 3 to 6 selected from Steareth-2, Steareth-3, Steareth-4, Ceteth-2, Ceteth-3, Ceteth-4, Myristeth-2, Myristeth-3, Myristeth-4, Laureth-2, Laureth-3, Laureth-4, Trideceth-2, Trideceth-3 and Trideceth-4 as well as mixtures thereof in a total amount of 1.8-3 wt %, preferably about 2-about 2.8 wt % and especially preferably about 2.4-about 2.6 wt %, each based on the total weight of the composition according to an exemplary embodiment.

Ethanol

Additional antiperspirant compositions that are preferred according to the present disclosure are characterized in that ethanol is present in an amount of about 0 to about 5 wt %, preferably about 0 to about 3 wt %, especially preferably about 0 to about 1 wt %, each based on the total weight of the composition.

Preferred antiperspirant compositions according to an exemplary embodiment are in the form of an oil-in-water emulsion.

Oils

Antiperspirant compositions preferred according to an exemplary embodiment contain at least one cosmetic oil, preferably in a total amount of about 0.1-about 15 wt %, especially preferably about 0.3-about 10 wt %, extremely preferably about 0.5-about 6 wt %, each based on the weight of the antiperspirant composition.

With the cosmetic oil, distinction is made between volatile and nonvolatile oils. Nonvolatile oils are understood to be oils, which have a vapor pressure of less than about 2.66 Pa (about 0.02 mmHg) at 20° C. and an ambient pressure of 1013 hPa. Volatile oils are understood to be oils, which have a vapor pressure of about 2.66 Pa-about 40,000 Pa (about 0.02 mmHg to about 300 mmHg), preferably about 13-about 12,000 Pa (about 0.1-90 mmHg), especially preferably about 15-about 3000 Pa, extremely preferably about 30-about 500 Pa at 20° C. and an ambient pressure of 1013 hPa.

Especially preferred nonvolatile non-silicone oils according to the present disclosure are selected from the addition products of at least 6 ethylene oxide units and/or propylene oxide units onto monovalent or polyvalent C3-22 alkanols such as butanol, butanediol, myristyl alcohol and stearyl alcohol, for example, PPG-13 butyl ether, PPG-14 butyl ether, PPG-9 butyl ether, PPG-10 butane diol, PPG-15 stearyl ether as well as mixtures thereof.

Particularly preferred compositions according to the present disclosure contain at least one cosmetic oil selected from PPG-13 butyl ether, PPG-14 butyl ether, PPG-9 butyl ether, PPG-10 butanediol, PPG-15 stearyl ether as well as mixtures thereof in a total amount of about 0.1-about 15 wt %, especially preferably about 0.3-about 10 wt %, extremely preferably about 0.5-about 6 wt %, each based on the weight of the total antiperspirant composition. Extremely preferred compositions according to the present disclosure contain about 0.1-about 15 wt %, especially preferably about 0.3-about 10 wt %, extremely preferably about 0.5-about 6 wt % PPG-15 stearyl ether, each based on the weight of the total antiperspirant composition according to an exemplary embodiment.

Additional preferred nonvolatile non-silicone oils according to the present disclosure include the esters of the linear or branched saturated or unsaturated fatty alcohols with 2-30 carbon atoms with linear or branched saturated or unsaturated fatty acids with 2-30 carbon atoms, which may be hydroxylated. Esters of the linear or branched saturated fatty alcohols with 2 to 5 carbon atoms with linear or branched saturated or unsaturated fatty acids with 10-18 carbon atoms, which may be hydroxylated are preferred. Preferred examples of these include isopropyl palmitate, isopropyl stearate, isopropyl myristate, 2-hexyldecyl stearate, 2-hexyldecyl laurate, isononyl isononanoate, 2-ethylhexyl palmitate and 2-ethylhexyl stearate. Also preferred are isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid 2-butyl octanoate, diisotridecyl acetate, n-hexyl laurate, n-decyloleate, oleyl oleate, oleyl erucate, erucyl oleate, C12-C15 alkyl lactate and di-C12-C13 alkyl malate as well as the benzoic acid esters of linear or branched C8-22 alkanols. Especially preferred are benzoic acid C12-C15 alkyl esters, for example, available as the commercial product Finsolv® TN (C12-C15 alkyl benzoate) as well as benzoic acid isostearyl esters that can be obtained, for example, as Finsolv® SB, 2-ethylhexyl benzoate, obtainable, for example, as Finsolv® EB, and benzoic acid 2-octyldodecyl ester that can be obtained, for example, as Finsolv® BOD. Triethyl citrate is another especially preferred ester oil.

Additional preferred nonvolatile non-silicone oils according to the present disclosure are selected from branched saturated or unsaturated fatty alcohols with 6 to 30 carbon atoms. These alcohols are frequently also referred to as Guerbet alcohols because they can be obtained according to the Guerbet reaction. Preferred alcohol oils include 2-hexyldecanol, 2-octyldodecanol and 2-ethylhexyl alcohol. Also preferred is isostearyl alcohol. Other preferred nonvolatile oils are selected from mixtures of Guerbet alcohols and Guerbet alcohol esters, for example, 2-hexyldecanol and 2-hexyldecyllaurate.

The expression "triglyceride," which is used below, means "glycerol triester." Additional nonvolatile oils preferred according to the present disclosure are selected from the triglycerides of linear or branched saturated or unsaturated optionally hydroxylated C8-30 fatty acids if these are liquid under normal conditions. The use of natural oils, for example, soy oil, cottonseed oil, sunflower oil, palm oil, palm kernel oil, linseed oil, almond oil, castor oil, corn oil, rapeseed oil, olive oil, sesame oil, thistle oil, wheat germ oil, peach kernel oil and the liquid fractions of coconut oil and the like may be particularly suitable. Especially preferred are the synthetic triglyceride oils, in particular capric/caprylic triglycerides, e.g., the commercial products Myritol® 318 or Myritol® 331 (BASF) with unbranched fatty acid radicals as well as glyceryl triisostearol and glyceryl tri(2-ethyl hexanoate) with branched fatty acid radicals. Such triglyceride oils preferably constitute less than about 50 wt % of the total weight of all cosmetic oils in the composition according to the present disclosure.

Additional nonvolatile non-silicone oils that are particularly preferred according to the present disclosure are selected from the dicarboxylic acid esters of linear or branched C2-C10 alkanols, in particular diisopropyl adipate, di-n-butyl adipate, di-(2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate and di-(2-hexyldecyl) succinate.

Additional nonvolatile non-silicone oils that are especially preferred according to an exemplary embodiment are selected from the addition products of 1 to 5 propylene oxide units onto monovalent or polyvalent C8-22 alkanols such as octanol, decanol, decanediol, lauryl alcohol, myristyl alcohol and stearyl alcohol, preferably PPG-2 myristyl ether and PPG-3 myristyl ether.

Additional preferred nonvolatile non-silicone oils according to the present disclosure are selected from the symmetrical, asymmetrical or cyclic esters of carbonic acid with C6-C20 alcohols, e.g., di-n-caprylylcarbonate or di-(2-ethylhexyl)carbonate. Esters of carbonic acid with C1-C5 alcohols, e.g., glycerol carbonate or propylene carbonate however are compounds that are not suitable as cosmetic oils.

Additional oils that may be preferred according to the present disclosure are selected from the esters of dimers of unsaturated C12-C22 fatty acids (dimer fatty acids) with monovalent linear branched or cyclic C2-C18 alkanols or with polyvalent linear or branched C2-C6 alkanols. Especially preferably the total weight of dimer fatty acid esters amounts to about 0.5-about 10 wt %, preferably about 1-about 5 wt %, each based on the total composition.

Volatile cosmetic oils are usually selected from cyclic silicone oils with the INCI designation cyclomethicone. The INCI designation cyclomethicone is understood to include in particular cyclotrisiloxane (hexamethylcyclotrisiloxane), cyclotetrasiloxane (octamethylcyclotetrasiloxane), cyclopentasiloxane (decamethylcyclopentasiloxane) and cyclohexasiloxane (dodecamethylcyclohexasiloxane). These oils have a vapor pressure of about 13-about 15 Pa at 20° C.

Cyclomethicones are known in the prior art as very suitable oils for cosmetic products, in particular for antiperspirant and deodorant products. Because of their persistence in the environment however it may be preferable according to the present disclosure to avoid the use of cyclomethicones. In a particularly preferred embodiment, the compositions according to the present disclosure contain zero to less than about 1 wt % cyclomethicone, based on the weight of the composition.

A preferred cyclomethicone substitute is a mixture of C13-C16 isoparaffins, C12-C14 isoparaffins and C13-C15 alkanes, whose viscosity at 25° C. is in the range of 2 to 6 mPas, and which have a vapor pressure at 20° C. in the range of about 100 to about 150 Pa. Such a mixture is available, for example, under the designation SiClone SR-5 from the company Presperse, Inc.

Additional preferred volatile silicone oils are selected from volatile linear silicone oils, in particular volatile linear silicone oils with 2 to 10 siloxane units such as hexamethyldisiloxane (L2), octamethyltrisiloxane (L3), decamethyltetrasiloxane (L4) such as those contained, for example, in the commercial products DC 2-1184, Dow Corning® 200 (about 0.65 cSt) and Dow Corning® 200 (about 1.5 cSt) from Dow Corning and low-molecular phenyl trimethicone with a vapor pressure of about 2000 Pa at 20° C. such as that obtainable, for example, from GE Bayer Silicones/Momentive under the brand name Baysilone Fluid PD 5.

In addition at least one volatile non-silicone oil may also be present. Preferred volatile non-silicone oils are selected from C8-C16 isoparaffins, in particular from isononane, isodecane, isoundecane, isododecane, isotridecane, isotetradecane, isopentadecane and isohexadecane as well as mixtures thereof. C10-C13 isoparaffin mixtures, in particular those with a vapor pressure of about 10-about 400 Pa at 20° C., preferably about 13-about 100 Pa are preferred.

Additional antiperspirant compositions in the form of oil-in-water emulsions that are preferred according to the present disclosure are characterized in that the at least one propylene glycol monoester of branched saturated C6-C30 alkane carboxylic acids is selected from propylene glycol monoisostearate, propylene glycol monoisopalmitate, propylene glycol monoisobehenate, propylene glycol monoisoarachinate, propylene glycol monoisomyristate, propylene glycol monoisocaprate, propylene glycol monoisocaprinate and propylene glycol monoisocaprylate as well as mixtures thereof. Additional antiperspirant compositions that are preferred according to the present disclosure in the form of oil-in-water emulsions are characterized in that the at least one branched saturated C10-C30 alkanol is selected from isostearyl alcohol, isocetyl alcohol, isomyristyl alcohol, isotridecyl alcohol, isoarachidyl alcohol, isobehenyl alcohol, isocapryl alcohol, isocaprinyl alcohol, isocaprylyl alcohol, as well as mixtures thereof.

Additional antiperspirant compositions that are preferred according to the present disclosure in the form of oil-in-water emulsions are characterized in that they contain at least one nonionic emulsifier with an HLB value in the range of about 3 to about 6 and at least one nonionic emulsifier with an HLB value in the range of about 12 to about 18.

Additional antiperspirant compositions in the form of oil-in-water emulsions that are preferred according to the present disclosure are characterized in that at least one nonionic emulsifier with an HLB value in the range of about 3 to about 6 is present in a total amount of about 1.8 to about 3 wt % and at least one nonionic emulsifier with an HLB value in the range of about 12 to about 18 is present in an amount of about 1 to about 2 wt %, wherein the amount values are each based on the total weight of the composition according to the present disclosure.

Additional antiperspirant compositions in the form of oil-in-water emulsions that are preferred according to the present disclosure are characterized in that they contain steareth-2 as the nonionic emulsifier with an HLB value in the range of about 3 to about 6, and at the same time, they contain steareth-21 as the nonionic emulsifier with an HLB value in the range of about 12 to about 18.

Additional antiperspirant compositions in the form of oil-in-water emulsions that are preferred according to the present disclosure are characterized in that they contain steareth-2, steareth-21 and PPG-15 stearyl ether.

Additives

In addition to the aforementioned ingredients, the compositions according to the present disclosure may also contain additional additives and excipients, which improve their stability, for example, such as preservatives, e.g., phenoxyethanol, methyl paraben or propyl paraben, antioxidants, e.g., tetradibutyl pentaerythrityl hydroxyhydrocinnamates, Lipochroman-6, tocopherol, tocopheryl acetate or ascorbic acid and derivatives thereof, vitamins and derivatives thereof such as tocopherol, tocopheryl acetate, ascorbic acid, panthenol or pantolactone, perfumes, essential oils, menthol and menthol derivatives, which have a cooling effect on the skin, active ingredients, which delay hair growth, for example, eflornithine or glycyrrhizin and derivatives thereof, polyols such as 1,2-propylene glycol, glycerol, 2-methyl-1,3-propanediol, 1,2-butylene glycol, 1,3-butylene glycol, 1,4-butylene glycol, pentylene glycols such as 1,2-pentanediol and 1,5-pentanediol, hexanediols such as 1,2-hexanediol and 1,6-hexanediol, hexanetriols such as 1,2,6-hexanetriol, 1,2-octanediol, 1,8-octanediol, dipropylene glycol, tripropylene glycol, diglycerol, triglycerol, erythritol, sorbitol, cis-1,4-dimethylolcyclohexane, trans-1,4-dimethylolcyclohexane, any isomer mixtures of cis- and trans-1,4-dimethylolcyclohexane, urea, N,N'-bis-(2-hydroxyethyl)urea, sodium pyrrolidone carboxylate, plant extracts, e.g., aloe vera extract, natural fats and oils such as jojoba oil, evening primrose oil or linseed oil, saturated and unsaturated fatty acids such as stearic acid, oleic acid, linoleic acid, linolenic acid or γ-linolenic acid, squalane, squalene, deodorant active ingredients such as silver salts, colloidal silver, zeolites, 2-benzylheptan-1-ol, anise alcohol, mixtures of 2-benzylheptan-1-ol and phenoxyethanol, 3-(2-ethylhexyloxy)-1,2-propanediol or tropolone, thickeners such as dehydroxanthan gum, celluloses, cellulose ethers and starch derivatives as well as mixtures of these substances.

Preferred compositions according to the present disclosure have a viscosity in the range of about 1000 to about 10,000 about mPas, preferably about 1500 to about 3000 mPas, wherein the viscosity is measured at 23° C. using a rotary viscometer from the company Brookfield, model RVF, spindle 4, shear rate (rotational frequency) of 20 min-1, without the Helipath.

Another subject matter of the present patent application is the nontherapeutic use of L-valine to improve the skin tolerability of an antiperspirant composition containing water and at least one antiperspirant aluminum-zirconium-glycine complex, wherein the weight rate of glycine to L-valine is in the range of about 20:1 to about 4:1.

Another subject matter of the present patent application is the nontherapeutic use of an antiperspirant composition containing water, at least one antiperspirant aluminum-zirconium-glycine complex and L-valine, wherein the weight ratio of glycine to L-valine is in the range of about 20:1 to about 4:1, for an antiperspirant treatment of the skin.

With respect to additional preferred embodiments of the applications according to the present disclosure, what was said regarding the antiperspirant compositions also applies here, mutatis mutandis.

Another subject matter of the present patent application is a nontherapeutic method for improving the skin tolerability of an antiperspirant composition containing water and at least one antiperspirant aluminum-zirconium-glycine complex, in which enough L-valine is added to this antiperspirant composition, so that the weight ratio of glycine to L-valine is in the range of about 20:1 to about 4:1.

Another subject matter of the present patent application is a nontherapeutic method for antiperspirant treatment of the skin, in which an antiperspirant composition containing water, at least one antiperspirant aluminum-zirconium-glycine complex and L-valine, in which the weight ratio of glycine to L-valine is in the range of about 20:1 to about 4:1, is applied to the skin.

With respect to additional preferred embodiments of the methods according to the present disclosure, what was already said regarding the antiperspirant compositions also applies here mutatis mutandis.

The tolerability of an antiperspirant composition on skin, wherein the composition contains water and at least one antiperspirant aluminum-zirconium-glycine complex without L-valine is significantly inferior to the skin tolerability of an aqueous antiperspirant composition containing the same amount and type of antiperspirant aluminum-zirconium-glycine complex and enough L-valine so that the weight ratio of glycine to L-valine is in the range of about 20:1 to about 4:1.

In summary the subject matter of the present disclosure is given by the following points:

Point 1 Antiperspirant composition, containing:
 a) water,
 b) at least one antiperspirant aluminum-zirconium-glycine complex,
 c) L-valine,
 characterized in that the weight ratio of glycine to L-valine is in the range of about 20:1 to about 4:1.

Point 2 Composition according to point 1, characterized by a pH in the range of about 3.0 to about 4.5, especially preferably in the range of about 3.3 to about 4.0, extremely preferably in the range of about 3.4 to about 3.8, each measured at 20° C.

Point 3 Composition according to point 1 or 2, characterized in that the at least one antiperspirant aluminum-zirconium-glycine complex is present in a total amount of about 6-about 20 wt %, preferably about 10 to about 16 wt %, especially preferably about 12 to about 14 wt %, each based on the total weight of the active substance (USP) without any water of crystallization or ligands present in the antiperspirant composition.

Point 4 Composition according to any one of points 1 to 3, characterized in that about 0.4 to about 5.0 wt %, preferably about 0.5 to about 2.0 wt %, especially preferably about 0.6-about 1.0 wt % glycine is present, each based on the weight of the antiperspirant composition.

Point 5 Composition according to any one of points 1 to 4, characterized in that about 0.01 to about 1 wt %, preferably about 0.05 to about 0.3 wt %, especially preferably about 0.1 to about 0.2 wt % L-valine is included, each based on the weight of the antiperspirant composition.

Point 6 Composition according to any one of points 1 to 5, characterized in that the weight ratio of glycine to L-valine is in the range of about 17:1 to about 5:1, preferably about 15:1 to about 10:1.

Point 7 Composition according to any one of points 1 to 6, characterized in that the ethanol is included in an amount of about 0 to about 5 wt %, preferably about 0 to about 3 wt %, especially preferably about 0 to about 1 wt %, each based on the weight of the composition.

Point 8 Composition according to any one of points 1 to 7, characterized in that at least one cosmetic oil is included, preferably in a total amount of about 0.1 to about 15 wt %, especially preferably about 0.3 to about 10 wt %, extremely preferably about 0.5 to about 6 wt %, each based on the total weight of all the additional oils in the antiperspirant composition.

Point 9 Composition according to any one of points 1 to 8, characterized in that water is contained in a total amount of about 40 to about 90 wt %, preferably about 50 to about 85 wt %, especially preferably about 60 to about 80 wt % each based on the weight of the composition.

Point 10 Composition according to any one of points 1 to 9, characterized in that the valine, in particular L-valine, is not present as part of or a ligand of an antiperspirant aluminum zirconium compounds but instead is dissolved freely in the composition according to an exemplary embodiment.

Point 11 Composition according to any one of points 1 to 10, characterized in that it is present in the form of an oil-in-water emulsion and at least one nonionic emulsifier with an HLB value in the range of about 3 to about 6 and at least one nonionic emulsifier with an HLB value in the range of about 12 to about 18 are included.

Point 12 Composition according to point 11, characterized in that at least one nonionic emulsifier with an HLB value in the range of about 3 to about 6 is included in a total amount of about 1.8-about 3 wt % and at least one nonionic emulsifier with an HLB value in the range of about 12 to about 18 is included in a total amount of about 1 to about 2 wt %, wherein the quantitative amounts are each based on the total weight of the composition according to an exemplary embodiment.

Point 13 Composition according to any one of points 11 or 12, characterized in that steareth-2 is included as a nonionic emulsifier with an HLB value in the range of about 3 to about 6, and at the same time, steareth-21 is included as a nonionic emulsifier with an HLB value in the range of about 12 to about 18.

Point 14 Nontherapeutic use of L-valine to improve the skin tolerability of an antiperspirant composition containing water and at least one antiperspirant aluminum-zirconium-glycine complex, wherein the weight ratio of glycine to L-valine is in the range of about 20:1 to about 4:1.

Point 15 Use according to point 14, characterized in that the antiperspirant composition is a composition according to any one of points 1 to 13.

The following embodiments should illustrate the subject matter of the present disclosure without restricting it to these.

The following roll-on emulsions of the oil-in-water type according to an exemplary embodiment were prepared (quantitative amounts in wt %):

|  | No. 1 | No. 2 | No. 3 | No. 4 | No. 5 |
|---|---|---|---|---|---|
| PPG-15 stearyl ether | 0.5 | 0.5 | 0.5 | 0.5 | 0.5 |
| Steareth-2 | 2.4 | 2.4 | 2.4 | 2.4 | 2.4 |
| Steareth-21 | 1.5 | 1.5 | 1.5 | 1.5 | 1.5 |
| Ultra ZAG 88 L (SummitReheis)* | 30.0 | 32.0 | 40.0 | — | — |
| AAZG 3109 (SummitReheis)** | — | — | — | 35.0 | — |
| AZG 364 (SummitReheis)*** | — | — | — | — | 40.0 |
| L-Valine | 0.1 | 0.15 | 0.3 | 0.2 | 1.0 |
| Water | to Σ 100 | to Σ 100 | to Σ 100 | to Σ 100 | to Σ 100 |
| pH (20° C.) | 3.5 | 3.6 | 3.3 | 3.5 | 3.0 |
| Glycine/L-valine weight ratio | 12-18 | 8.53-11.3 | 5.3-7.1 | 6.0-8.0 | 4.2-5.4 |

*Ultra ZAG 88 L Aluminum zirconium tetrachlorohydrex GLY, 30 to 34 wt % aluminum-zirconium-glycine complex, 63 wt % water, glycine 4.0-5.3 wt %
**AAZG 3109 Aluminum zirconium octachlorohydrex GLY, 27.7 to 30.5 wt % aluminum-zirconium-glycine complex, 64.09-67.59 wt % water, Al:Zr ratio (molar): 8.5:1-10.0:1, $CaCl_2$: 4.71-5.41 wt %; glycine 3.4-4.6 wt %
***AZG 364 Aluminum zirconium tetrachlorohydrex GLY (powder), 72-85 wt % aluminum-zirconium-glycine complex, MD 44 μm, glycine: 10.5-13.5 wt %, Al:Zr ratio (molar): 3.4:1-3.8:1

After application of the antiperspirant compositions according to an exemplary embodiment to the skin, in particular nos. 1 to 5, a reduction in perspiration of about 60 to about 85% was achieved, while at the same time, the compositions were tolerated very well by the volunteers in comparison with antiperspirant compositions containing no L-valine as well as in comparison with antiperspirant compositions containing L-valine, in which the weight ratio of glycine to L-valine was outside the range of about 20:1 to about 4:1.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An antiperspirant composition, comprising:
    water,
    at least one antiperspirant aluminum-zirconium-glycine complex, and
    L-valine,
    wherein the weight ratio of glycine to L-valine is from about 20:1 to about 4:1.

2. The composition according to claim 1, the antiperspirant composition has a pH of from about 3.0 to about 4.5 at 20° C.

3. The composition according to claim 1, wherein the at least one antiperspirant aluminum-zirconium-glycine complex is present in a total amount of from about 6 to about 20 wt % based on the total weight of the active substance (USP) without any water of crystallization or ligands present in the antiperspirant composition.

4. The composition according to claim 1, wherein from about 0.4 to about 5.0 wt % glycine is present based on the weight of the antiperspirant composition.

5. The composition according to claim 1, wherein from about 0.01 to about 1 wt % L-valine is included based on the weight of the antiperspirant composition.

6. The composition according to claim 1, wherein the weight ratio of glycine to L-valine is from about 17:1 to about 5:1.

7. The composition according to claim 1, wherein ethanol is included in an amount of from about 0 to about 5 wt % based on the weight of the composition.

8. The composition according to claim 1, wherein at least one cosmetic oil is included in a total amount of from about 0.1 to about 15 wt % based on the total weight of all the additional oils in the antiperspirant composition.

9. The composition according to claim 1, wherein water is included in a total amount of from about 40 to about 90 wt % based on the weight of the composition.

10. A method comprising using L-valine to improve skin tolerability of an antiperspirant composition comprising:
water and at least one antiperspirant aluminum-zirconium-glycine complex, wherein the method comprises incorporating the L-valine into the antiperspirant composition such that the weight ratio of glycine to L-valine is from about 20:1 to about 4:1.

11. The composition according to claim 1, wherein the antiperspirant composition has a pH of from about 3.3 to about 4.0 at 20° C.

12. The composition according to claim 1, wherein the at least one antiperspirant aluminum-zirconium-glycine complex is present in a total amount of from about 10 to about 16 wt % based on the total weight of the active substance (USP) without any water of crystallization or ligands present in the antiperspirant composition.

13. The composition according to claim 1, wherein from about 0.5 to about 2.0 wt % glycine is present based on the weight of the antiperspirant composition.

14. The composition according to claim 1, wherein from about 0.05 to about 0.3 wt % L-valine is included based on the weight of the antiperspirant composition.

15. The composition according to claim 1, wherein the weight ratio of glycine to L-valine is from about 15:1 to about 10:1.

16. The composition according to claim 1, wherein ethanol is included in an amount of from about 0 to about 3 wt % based on the weight of the composition.

17. The composition according to claim 1, wherein at least one cosmetic oil is included in a total amount of from about 0.3 to about 10 wt % based on the total weight of all the additional oils in the antiperspirant composition.

18. The composition according to claim 1, wherein water is included in a total amount of from about 50 to about 85 wt % based on the weight of the composition.

* * * * *